(12) United States Patent
Gao et al.

(10) Patent No.: US 7,604,930 B1
(45) Date of Patent: Oct. 20, 2009

(54) METHODS AND DEVICES FOR CRYOPRESERVATION OF BIOLOGICAL CELLS AND TISSUES

(75) Inventors: Dayong Gao, Lexington, KY (US); Gary Van Zant, Lexington, KY (US); XiangDong Cui, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 230 days.

(21) Appl. No.: 11/007,096

(22) Filed: Dec. 8, 2004

Related U.S. Application Data

(63) Continuation of application No. 10/206,538, filed on Jul. 26, 2002, now abandoned.

(60) Provisional application No. 60/307,991, filed on Jul. 26, 2001, provisional application No. 60/308,450, filed on Jul. 27, 2001.

(51) Int. Cl.
*A01N 1/02* (2006.01)
*A01N 65/00* (2006.01)
(52) U.S. Cl. .................... 435/2; 424/93.72
(58) Field of Classification Search .......... None
See application file for complete search history.

(56) References Cited

U.S. PATENT DOCUMENTS

| | | | | |
|---|---|---|---|---|
| 4,251,995 A | * | 2/1981 | Pert et al. | 62/60 |
| 4,469,227 A | * | 9/1984 | Faust | 206/527 |
| 5,795,711 A | * | 8/1998 | Mullon et al. | 435/1.1 |
| 5,863,715 A | * | 1/1999 | Rajotte et al. | 435/1.3 |

* cited by examiner

*Primary Examiner*—Sandra E Saucier
(74) *Attorney, Agent, or Firm*—King & Schickli, PLLC

(57) ABSTRACT

Novel methods, compositions, and devices for achieving optimal cooling of living cells during cryopreservation are disclosed. In one aspect, the method comprises gradually cooling the cell to a first predetermined temperature, followed by rapidly cooling the cell to a second predetermined temperature. In another aspect, a device is described for achieving a desired cooling rate for a cell, comprising a first container for holding a cell, a second container for holding the first container, and optionally a frame for holding the first container in a spaced apart relationship with the second container. The method of the invention comprises placing cells into the first container, placing the first container in the second container and sealing the second container, and placing the second container in a suitable cooling device. In yet another aspect, novel cryoprotectant compositions are provided comprising conventional cryoprotectant plus one or more high molecular weight cryoprotectants.

8 Claims, 9 Drawing Sheets

METHODS AND DEVICES FOR CRYOPRESERVATION OF BIOLOGICAL CELLS AND TISSUES

This application claims the benefit of U.S. Provisional Patent Application Ser. Nos. 60/307,991, filed on Jul. 26, 2001 and 60/308,450, filed on Jul. 27, 2001, both of which are incorporated herein by reference, and is a continuation of U.S. patent application Ser. No. 10/206,538, filed on Jul. 26, 2002, now abandoned the entirety of which is also incorporated herein by reference.

TECHNICAL FIELD

The present invention relates to devices and methods for optimal cryopreservation of biological cells and tissues, and to cryoprotectant compositions. The invention further relates to devices and methods for accomplishing controlled cooling of various cell types during cryopreservation, maintaining optimal cooling rates according to specific cell types being cryopreserved.

BACKGROUND OF THE INVENTION

Cryopreservation of different cell types is critically influenced by cooling rate and cryoprotectant. Overly fast cooling rates can cause lethal intracellular formation of ice crystals. At the other end of the spectrum, overly slow cooling rates can result in osmotic shock injury to cells. Further, conventional cryoprotectants, while essential to the successful freezing of cells, are often toxic to the same cells in the thawed state.

Research has shown that for most biological cells, there is a specific cooling rate that may be considered optimal for the cell type. For example, for human hematopoietic progenitor cells (HPCs) the optimal cooling rates are known to be from about 1° C./min. to about 3° C./min. Currently utilized commercial devices for cooling cells for cryopreservation accomplish controlled temperature changes by injecting liquid nitrogen vapor through an electromagnetic valve. As the temperature inside the devices increases or decreases, additional liquid nitrogen is injected to maintain the desired cooling rate.

Disadvantageously, these cooling devices are expensive, require high rates of liquid nitrogen vapor consumption, and are unreliable due to the relative fragility of the required electromagnetic valves. Accordingly, there is a need in the art for inexpensive, reliable devices for maintaining narrowly tailored, optimal cooling rates for various cell types to be cryopreserved.

It is desirable to maintain stores of a variety of cell types, some of which may be relatively fragile cells, for future use. For example, platelets, particularly human platelets, are in wide demand for a variety of uses requiring hemostasis such as standard transfusions in case of illness or trauma, chemotherapy, bone marrow transplants, and the like. The most common method for storage of platelets and certain other fragile cell types in, for example, blood banks, is so-called liquid storage, wherein platelets are maintained in liquid solutions at room temperature for a maximum of 5 days, and discarded if not used. Attempting longer-ten storage of platelets under such conditions results in progressive platelet aging and cytokine secretion, and risks microbial contamination. Further, screening processes for ensuring that donor platelets are immunologically compatible with prospective transfusion candidates may require 3-5 days to complete, further shortening the window of usefulness for stored platelets. Finally, there is currently no means for patients to store autogeneic platelets for long periods of time for future use.

Cryogenic preservation of cells is commonly employed when long-term storage of such cells is desirable. However, at present there are no reliable cryopreservation techniques for fragile cell types such as platelets which avoid the problems of loss of, e.g. viability, ability to secrete cytokines, and membrane stability. Accordingly, there is a need in the art for methods and devices for cryopreservation of cells, particularly fragile cells such as platelets and hematopoietic stem cells, which are reliable and do not result in cell damage and losses in viability. The present invention satisfies this need in the art by providing a method for cryopreservation of cells. The invention further provides devices suitable for cryopreservation of cells, including fragile cells, in accordance with the methods described.

SUMMARY OF THE INVENTION

In accordance with the purposes of the present invention as described herein, in one aspect of the present invention a method for cryopreservation of a living cell, particularly a fragile cell type, is provided, comprising placing the cell in a cryoprotectant having a cryoprotectant agent, gradually cooling the living cell in cryoprotectant to a first predetermined temperature, and rapidly cooling the living cell in cryoprotectant from the first predetermined temperature to a second predetermined temperature. The step of gradually cooling the cell may include cooling at a rate of between about 1° C./minute and about 3° C./minute. The first predetermined temperature may be between about −30° C. and about −40° C. Typically, the first predetermined temperature is about −30° C. The second predetermined temperature may be between about −80° C. and about −196° C. The rapid cooling step may be accomplished by immersing the cells and cryoprotectant in liquid nitrogen. Suitable cryoprotectants may be selected from a group consisting of dimethyl sulfoxide, polyvinylpyrrolidine, polyethylene glycol and mixtures thereof. The method of the invention is particularly suited for cryopreservation of a fragile cell type, for example a platelet or a hematopoietic stem cell.

In another aspect, a method for cryopreservation of a living cell is provided, comprising placing the living cell in a cryoprotectant including a cryoprotectant agent into a first container and sealing the first container. The first container including the living cell and cryoprotectant may then be placed into a second container, and the second container sealed. An insulating space is preserved between the first and second containers by any suitable means, such as by placing the first container in a rack prior to insertion into the second container.

The next step is gradually cooling the living cell in cryoprotectant at a rate of about 1° C./minute to about 3° C./minute to a desired temperature, typically −80° C. For longer term storage, the living cell may then be rapidly cooled to a second predetermined temperature, such as by immersing in liquid nitrogen.

The first and second containers may be constructed of any suitable material. Typically, the first container will be constructed of aluminum. The second container will typically be constructed of stainless steel. However, as will be described in greater detail below, it will be appreciated that the materials of which the first and second containers are constructed may be varied in accordance with the desired heat transfer properties to achieve a specific, predetermined cooling rate.

In yet another aspect, the present invention provides an apparatus for accomplishing the aforesaid method and holding living cells for cooling during cryopreservation, comprising a first container for receiving and holding the living cells and a second container for receiving and holding the first container. The second container may be sealed around the first container to define a space between the exterior wall of the first container and the interior wall of the second container. Typically, this space will be air-filled. However, it will be appreciated that other materials having greater or lesser insulating properties may be used in accordance with the desired cooling rate achievable with the device. Typically, the first container may be constructed from aluminum and the second container may be constructed from stainless steel. However, the materials of which the first and second containers are constructed may be varied in accordance with the desired heat transfer properties to achieve a specific, predetermined cooling rate. For example, if a faster cooling rate is desired, a second container constructed entirely or partially from copper may be used.

In still yet another aspect of the present invention, a novel cryoprotectant composition for cryopreservation of a cell is provided, comprising conventional cryoprotectant agents in combination with high molecular weight cryoprotectant agents. The cryoprotectant agents may be selected from the group consisting of dimethyl sulfoxide, polyvinylpyrrolidine, polyethylene glycol, and any mixture thereof. Typically, the cryoprotectant of the present invention comprises dimethyl sulfoxide mixed with polyvinylpyrrolidine, polyethylene glycol, or mixtures of polyvinylpyrrolidine and polyethylene glycol. In one embodiment, the cryoprotectant may include about 0.5 to about 1.0 M dimethyl sulfoxide mixed with about 5.0 to about 15% (w/v) polyvinylpyrrolidine, typically 10%. In another embodiment, the cryoprotectant may include about 0.5 to about 1.0 M dimethyl sulfoxide mixed with about 0.1 to about 4% (w/v) polyethylene glycol, typically 2.0%.

Other objects and applications of the present invention will become apparent to those skilled in this art from the following description wherein there is shown and described a preferred embodiment of this invention, simply by way of illustration of the modes currently best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification illustrates several aspects of the present invention and, together with the description, serves to explain the principles of the invention. In the drawing.

Figure 1:
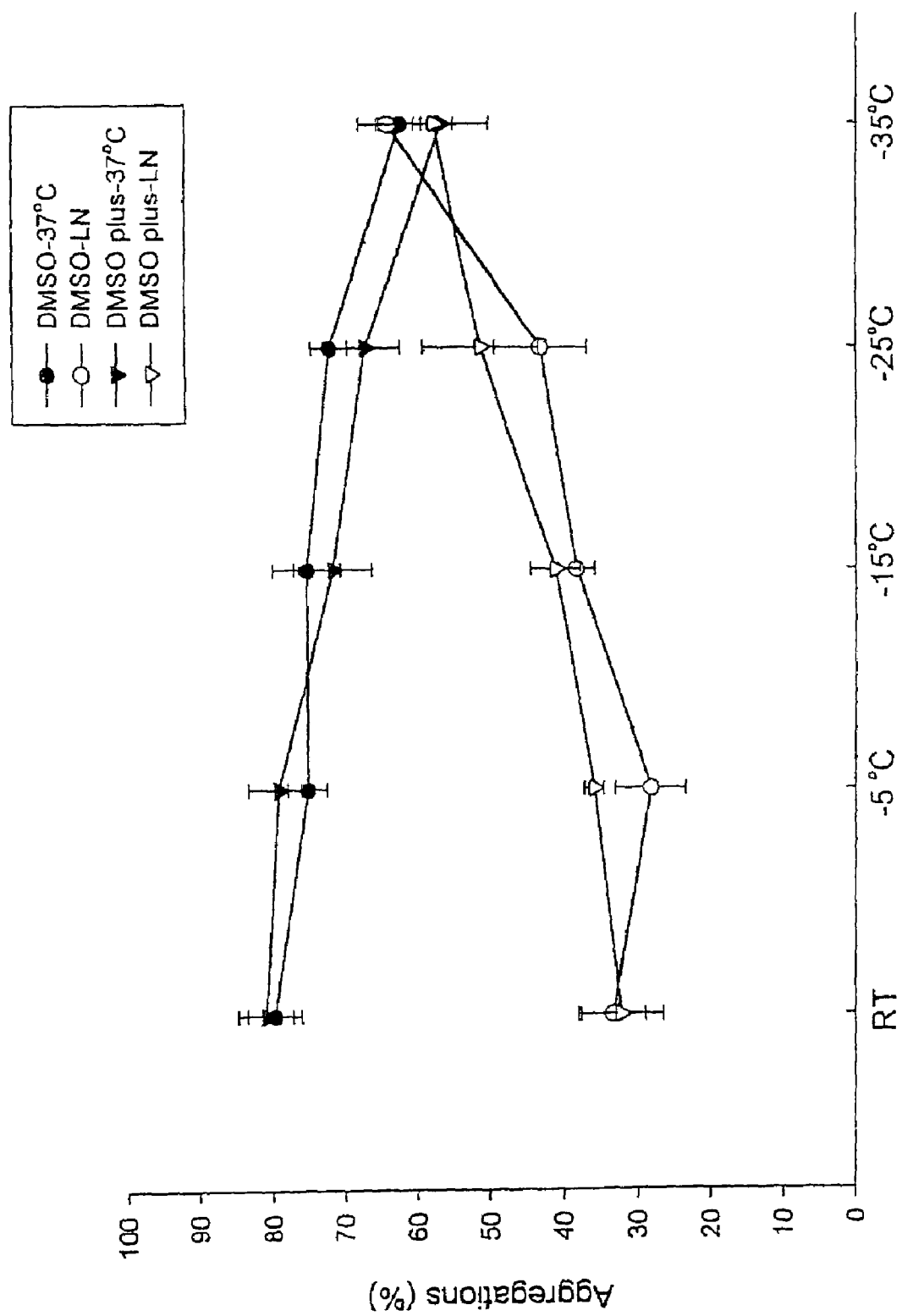
FIG. 1 shows aggregation of platelets following freezing to different temperatures, with or without immersion in liquid nitrogen. The cryoprotectant used was 1 M DMSO.

Reference will now be made in detail to the presently preferred embodiments of the invention, examples of which are illustrated in the accompanying drawing.

DETAILED DESCRIPTION OF THE INVENTION

In one aspect, the present invention provides a method for cryopreservation of various fragile cell types, including a graduated cooling rate method wherein cells are cooled to a desired first predetermined temperature, then placed directly into a commonly used freezing medium such as liquid nitrogen. In another aspect, the present invention provides a combination of cryoprotectants which optimize freezing of fragile cell types while minimizing the known cytotoxic effects of certain cryoprotectants on thawed cell preparations.

Example 1

Human platelet concentrates (up to 1 day in age) were obtained and kept at 22 C with continuous agitation in modified Tyrode's buffer solution and mixed (1:1) with 1 M dimethyl sulfoxide (DMSO) as cryoprotectant. Paired aliquots of platelet concentrates in vials were cooled in a BioCool system (BCIV40, Stone Ridge, N.Y.) at a cooling rate of 1 C/min. to −5, −15, −20, −25, −30, −35, and −40° C. At −5° C., a metal probe precooled in liquid nitrogen was used to induce ice seeding in the vials in a manner known in the art to prevent uncontrolled formation of ice crystals, and cooling was continued. Upon reaching the predetermined temperature as noted supra, one aliquot of platelet concentrate was transferred directly to liquid nitrogen (temperature −196 C), while the other aliquot of the pair was thawed in a 37 C water bath in accordance with standard methodology for thawing cryopreserved cells. After 10 minutes to allow the liquid nitrogen boiling phenomenon to dissipate, the second paired aliquot of platelet concentrate was similarly thawed at 37 C. After thawing, platelet function was evaluated as noted infra.

Following freezing and thawing experiments as noted above, platelets were evaluated for complete counts by microscopy and particle counter (Coulter Counter, Z M, Luton, England), for release of lactate dehydrogenase (LDH) by spectrophotometry using a kit in accordance with the manufacturers directions (Sigma, St. Louis, Mo.), and for platelet aggregation by aggregometer in accordance with the manufacturers directions (PACKS-4, platelet aggregation chromogenic system, Helena Laboratories, Beaumont, Tex.) in response to the agonists propyl gallate (0.03 mM), ADP (20 µM), epinephrine (300 µM), ristocetin (1.5 mg/ml), and collagen (10 µg/ml).

Fresh human platelet sample counts were $1.83$-$2.89 \times 10^9$/ml. After freeze-thawing, cell numbers declined slightly ($1.67$-$2.62 \times 10^9$/ml), or slightly better than 90% recovery ($90.05\% \pm 2.75$) (n=10, $P>0.05$).

Figure 2:
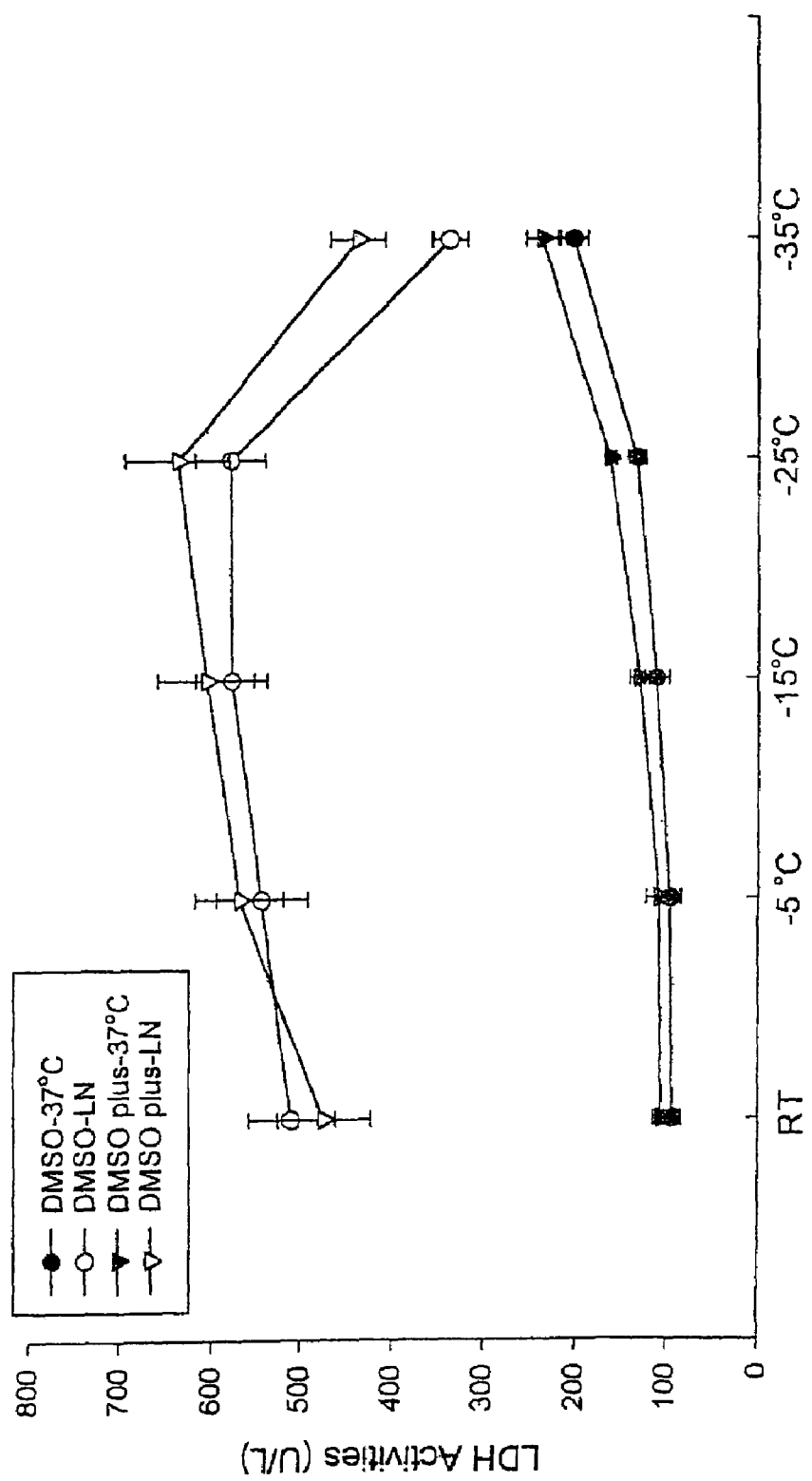
FIG. 2 shows release of LDH by platelets following freezing to different temperatures, with or without immersion in liquid nitrogen.

Cooling of platelet concentrate in 1 M. DMSO resulted in decreased percent platelet aggregation and increased LDH release. As seen in FIGS. 1 and 2, the freeze-thawing experiments showed that the intracellular ice formation point was between −30 C and −35 C.

Figure 3:
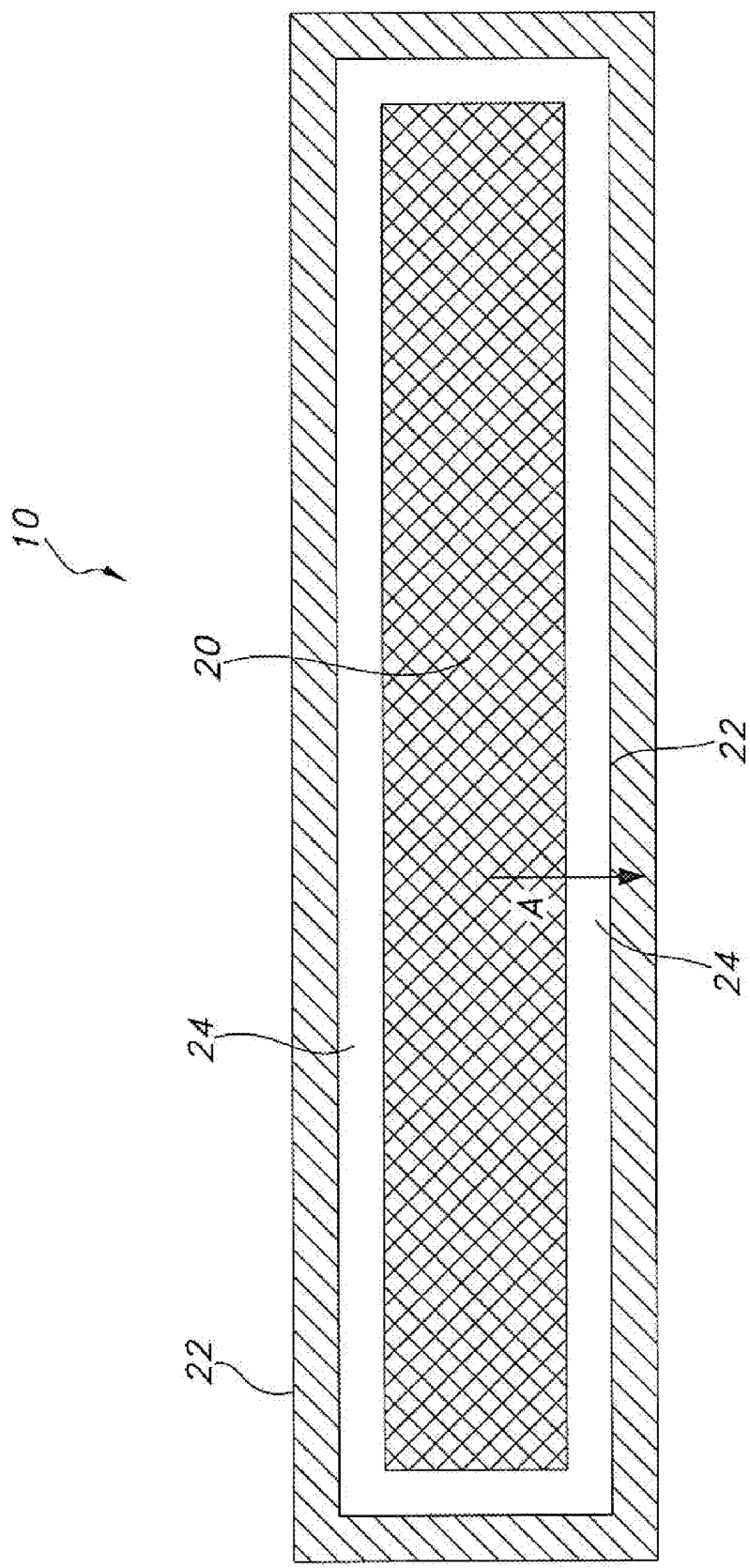
FIG. 3 is a schematic representation of the device for cooling a cell at a desired rate.

In another aspect of the present invention, a method and device for achieving an optimal cooling rate during cryopreservation in accordance with the needs of a particular cell type is described. The device is robust, reliable, and significantly less expensive than currently employed devices for cooling cells during cryopreservation. As best visualized schematically in FIG. 3, the cooling system 10 of the present invention comprises a first container 20 for holding cells or a bag holding a suspension of cells, a second container 22 into which one or more first containers 20 may be placed, and a cover (not shown for convenience) for sealing the second container 22 with the first container 20 therein. A frame (not shown for purposes of convenience) capable of slidably receiving the first container 20 may also be provided to increase ease of handling of multiple first containers 20. As shown schematically in FIG. 5, the frame also maintains the first container 20 and second container 22 in a spaced-apart relationship, providing a space 24 therebetween. Typically, space 24 will be air-filled. However, it should be appreciated that any suitable insulating material may be used to fill space 24, for example when a slower cooling rate is desired with use the cooling system 10 of the present invention. Heat exchange between air and chamber wall is caused by natural convection. Heat flux flows vertically through the chamber wall along the direction indicated by arrow A.

Example 2

In accordance with the methods of the invention, living cells at room temperature are placed in a standard blood bag with cryoprotectant (600 ml of cell suspension in a final concentration of 10% DMSO in buffer). The blood bags are then placed in a first, aluminum container. One or more first aluminum containers are then inserted into a metal frame and the frame is inserted into a second container and covered. In a presently preferred embodiment, the second container is constructed of stainless steel. The second, stainless steel container is then placed into a suitable cooling device, typically a −80° C. freezer of known design. In this fashion, a controlled cooling rate is achieved, allowing cryopreservation of cells without fear of damage from ice crystal formation or osmotic shock injury.

Example 3

The effects of varying parameters of the method and device of the present invention were evaluated. The parameters evaluated were: (1) concentration of cryoprotectant [dimethyl sulfoxide (DMSO)]; (2) wall thickness of the second, stainless steel bag; (3) sample mass/volume; and (4) surrounding temperature to which the device of the invention is exposed.

Sixty ml samples of phosphate-buffered saline (PBS) containing varying concentrations of DMSO were placed in blood bags of a type known in the art. The blood bags containing PBS/DMSO were placed into the device of the instant invention as described in Example 2, and the entire device of the instant invention was then placed in a freezer at −80° C. Temperature histories at different locations within the first, aluminum bag, the second, stainless steel bag, and the blood bag containing PBS/DMSO were recorded using thermocouples. The experiment continued until the temperature in all samples reached −80° C.

Figure 4A:
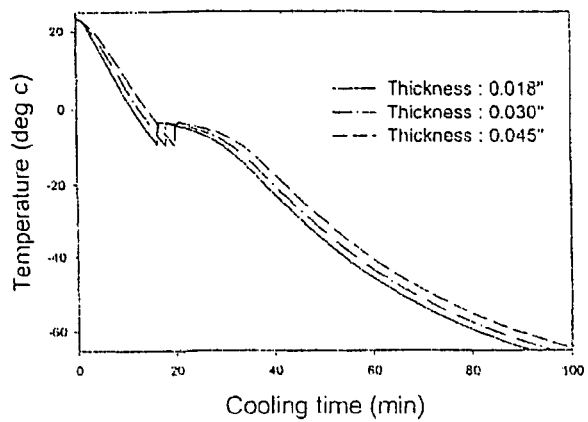
FIGS. 4a and 4b show calculated temperature histories of PBS/DMSO mixtures contained within the device of FIG. 3; (a) calculated temperature within sample as a function of varying second container wall thickness; (b) calculated temperature within sample as a function of varying freezer temperature
Figure 4B:
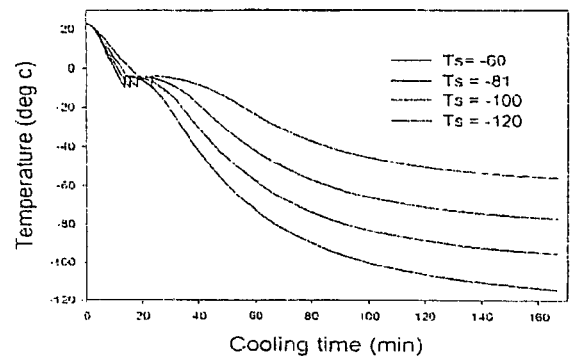

As seen in FIG. 4a, varying the wall thickness of the second, stainless steel bag allowed varying the cooling rate. The rate of cooling was inversely proportional to the thickness of the wall, i.e. the thinner the wall, the more rapid the rate of cooling. Similarly, the cooling rate increased greatly with the decreasing temperature within the freezer (FIG. 4b). Sample size and concentration of cryoprotectant did not significantly affect cooling rate. It will therefore be appreciated that it is possible to vary the rate of cooling to a desired rate by varying the wall thickness of the second container 22 and/or the temperature at which the freezer is set, allowing establishment of a predetermined rate of cooling in accordance with the specific requirements of the cells being cryopreserved. Thus, the present invention also provides a method of optimizing cooling conditions, i.e. the cooling rate of cells being cryopreserved, according to the specific needs of the cell type of interest.

Based on heat transfer principles, the chamber wall with a convective heat transfer boundary condition may be considered as a unit whose interior temperatures are nearly uniform if the following condition is satisfied $$\text{Biot's number}^{Bi=\frac{hL}{K}<0.1}$$

where h is the convective heat transfer coefficient of the fluid, $k_w$ is the thermal conductivity of stainless steel, and L is the specified length of the second container wall. The above equation indicates that to ensure that the thermal properties of the device of the present invention, internal conductive resistance should be much smaller than its external convective resistance. The mathematical formulation of an Energy conservation equation of the second container wall can be shown as below $$-E_{out} = E_{st}$$

Where $E_{out}$ is the heat loss of the second container wall, and $E_{st}$ is the internal energy change of chamber wall.

Accordingly, $$m_w c_w \frac{dT_0(t)}{dt} = q \qquad (1)$$
$$q = -hA_s(T_s(t) - T_s) - q_1$$
$$T_o(0) = T_0$$

Where $m_w$ is the mass of the second container wall, $c_w$ is the specific heat of stainless steel, $T_o(t)$ represents the temperature of the second container wall at different times, t represents the time, q is the net heat flux into chamber wall, $A_s$ is the surface area of chamber wall, $T_s$ is the surrounding temperature, $q_1$ is the heat flux from the aluminum first container into the second container wall, and $T_0$ is the temperature at initiation of freezing.

The convective heat exchange coefficient can be calculated as $$h = \frac{\overline{Nul}K_l}{l} = \frac{K_l}{l} F(Ral)$$
$$Ral = \frac{g\beta(T_0(t) - T_s)}{v\alpha}$$

Where Ral is Raleigh's number, F(Ral) is the empirical function of outside surface convection, g is the gravity acceleration, $\beta$ is the ratio of air volume expansion to temperature, $\nu$ is the dynamic viscosity of air, and $\alpha$ is the thermal diffusivity of air.

In accordance with the method of this invention, a first aluminum container containing living cells in cryoprotectant is placed inside the second, stainless steel container. The first container/cells exchange heat with the second container wall through an air layer between the first container and the second container wall. The conductive resistance of the air layer is much larger than the first container's internal conductive resistance. Accordingly, the heat transfer properties of the first canister and the cell samples may be combined in the calculations. The model may be expressed as:

$$\frac{d(m_s c_s T_i(t))}{dt} = q_1 \tag{2}$$

$$q_1 = \frac{T_0(t) - T_i(t)}{R_{con}}$$

$$T_i(0) = T_0$$

Where $T_i(t)$ is the temperature inside the first container, $R_{con}$ is the thermal resistance of the air layer, and $m_s c_s$ is the heat capacity of the cell samples inside the first container. Accordingly:

$$m_s c_s = m_a c_a + m_p c_p + m_c c_c + m_n c_n + m_h c_h$$

Where $m_a c_a$, $m_p c_p$, $m_c c_b$, $m_n c_n$, $m_h m_h$ are the heat capacities of the aluminum canister, freezing bag, CPA, salt and water respectively.

$$c_h = (1 - f(T_2))Cpl + f(T_2)Cps - \frac{df(T_2)}{dT_2} L_f(T_2)$$

From Kirchoff's Equation:

$$\left(\frac{\partial L_f}{\partial T_2}\right)_p = Cpl - Cps$$

$$L_f(T_2) = (Cpl - Cps)T_2 + L_f^0 \quad (T_2 = 0°C.)$$

Where Cpl and Cps are the specific heats of liquid water and ice respectively, $f(T_2)$ is the fraction of ice, $L_f(T_2)$ is the latent heat of water solidification at $T_2$ and $L_f^0$ is the latent heat of water solidification at 0° C.

The frozen fraction of water, $f(T_2)$ in the water-NaCl-DMSO solution during freezing process can be derived from the analytical equations describing the phase diagrams of the ternary solution:

$$f(T_2) = \left(1 + \frac{W_{T0}}{W_{H0}}\right) - \frac{W_{T0}}{W_{H0} W(T_2)}$$

Where $W(T_2)$ is the solution of the equation shown below:

$$T = A[100W(T_2)] + B[100W(T_2)]^2 + C[100W(T_2)]^3$$

$$A = -0.6 + 0.17 arctg(R)$$

-continued $$B = \frac{arctg(R/2)}{132} - 0.001$$

$$C = -4.5 \times 10^{-4}$$

$$W_{T0} = W_N + W_D = 1 - W_H$$

$$R = W_D / W_N$$

Where $W_D$, $W_N$ and $W_{H0}$ are the initial mass fractions of $Me_2SO$, salt and water in water-NaCl-$Me_2SO$ solution respectively, and $W(T_2)$ the solute mass fraction in solution at $T_2$.

In a water-NaCl-glycerol ternary system, the fraction of frozen water $f(T_2)$ may be expressed as:

$$f(T_2) = \left[1 + \frac{W_G}{W_{H0}}\right] - \left(\frac{W_G}{W_{H0}}\right) \cdot \frac{2}{a + (a^2 - 0.04T)^{0.5}}$$

$$a = \frac{1}{-1.6 - 1.27R - 0.25R^2}$$

$$R = \frac{W_G}{W_N}$$

Where $W_G$ is the glycerol mass fraction of the solution.

Equations (1) and (2) were discretized and calculated coupledly stepwise in response to time step interval. The following conditions were assumed in the calculation:

(1) Time step interval: 0.1 second (2) Initial sample temperature: T(0)=22° C.

(3) solution supercooling temperature is 0° C. (this is derived from experimental results)

(4) Thermophysical properties of the materials used in the calculation change with the temperature change.

According to these conditions, Biot's number was estimated as $$Bi = \frac{hL}{K_l} \approx 0.00059 << 0.1 \tag{3}$$

and the ratio of the internal thermal resistance of the first container to the air layer between the first container and the second container wall ($r_{in}/r_{air}$) was $$(r_{in}/r_{air}) 0.01 << 0.1 \tag{4}$$

Formulas (3) and (4) indicate that the thermal properties of the second container wall and the first container may be combined according to the conditions used in this calculation.

Effects of four factors on the sample temperature history in water-NaCl-DMSO were calculated:

(1) DMSO concentration (2) Thickness of stainless steel bag wall (3) HPCs sample mass/volume (4) Surrounding temperature inside the freezer It will therefore be appreciated that, using the calculations as described above, it is possible using known thermal transfer properties of any material to design devices in accordance with the present invention which maintain a specific, optimal cooling rate for a particular cell type. Optimal cooling rates for any cell type may be obtained from the literature, or may be determined experimentally by known methods. Accordingly, in yet another aspect of the present invention, a software program allowing selection of specific elements of the present invention as described above is provided to tailor the device of the invention to the specific cooling rate requirements of particular cell types. The software predicts an optimal cooling rate for a particular fluid system using known heat transfer principles and mathematical formulae as described above incorporating heat transfer properties of: (1) the first container; (2) the fluid(s) (with cells) contained in the first container; (3) the second container: (4) the air between the first and second containers; and (5) the dimensions of the second container. The software program of the present invention allows prediction of cooling rates in accordance with the above factors, and therefore is able to predict the cooling rate achievable with the device of the instant invention as described supra regardless of the dimensions of the device, materials used to construct the device, and the like.

Example 4

Figure 5:
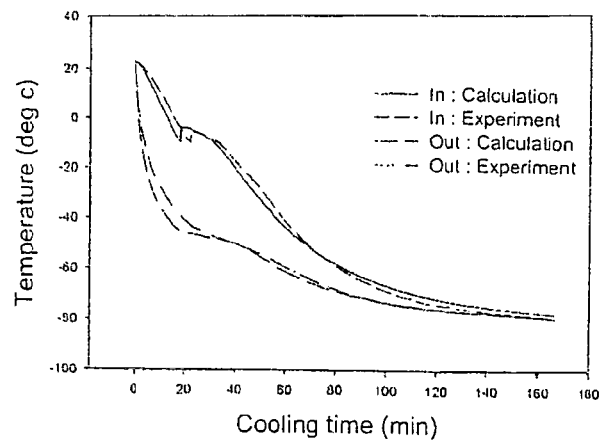
FIG. 5 shows the predicted temperature histories within sample bags (In) and at a wall of the second container of the device of this invention (Out) compared to calculated histories.

A device for cooling a cell was constructed as described above, comprising an aluminum first container 20, a stainless steel second container 22, a frame for holding first container 20 inside second container 22, and a cover for second container 22. Conventional blood bags containing PBS plus 10% DMSO were placed in first containers 20, the first containers 20 were placed in the second container 22 and into a −80° C. freezer. The second container 22 had a wall thickness of 0.03 inches. Temperatures at varying locations within the device were recorded using thermocouples as described in Example 3. Predicted temperatures were obtained using the software program of the present invention. As shown in FIG. 5, the software program of the present invention accurately predicted temperature histories for the PBS/DMSO samples, as well as for the second container wall.

It will therefore be appreciated that this software program allows the user to design a device in accordance with the method of the instant invention of specific dimensions, materials, etc. to achieve a cooling rate optimal for the particular cell type to be cryopreserved. For example, a copper second container could be used to achieve a more rapid cooling rate. An insulating material, such as styrofoam or any other insulating polymer, could be used to fill the airspace between the first and second containers to reduce the cooling rate. Regardless, upon input of the proper parameters as described above, the proper device may be designed using the software of this invention to achieve the desired cooling rate.

Accordingly, the method and device of the present invention provides a reliable, effective means for achieving a desired cooling rate during cryopreservation, minimizing the risk of damage to cells from osmotic shock injury or intracellular ice crystal formation. The method is suitable for cryopreservation of any cell type, including fragile cells such as bone marrow/cord blood hematopoietic progenitor cells for cancer treatment and gene therapy, for tissue cryopreservation for transplantation, for sperm/oocyte preservation for artificial insemination and in vitro fertilization, for cryopreservation of cell lines for research, and the like.

In still yet another aspect of the present invention, a novel cryoprotectant composition for cryopreservation of a cell is provided, comprising conventional cryoprotectant agents in combination with high molecular weight cryoprotectant agents. The cryoprotectant agents may be selected from the group consisting of dimethyl sulfoxide, polyvinylpyrrolidine, polyethylene glycol, and any mixture thereof. Typically, the cryoprotectant of the present invention comprises dimethyl sulfoxide mixed with polyvinylpyrrolidine, polyethylene glycol, or mixtures of polyvinylpyrrolidine and polyethylene glycol.

Example 5

Human platelet concentrates (up to 1 day in age) were obtained and kept at 22 C with continuous agitation in modified Tyrode's buffer solution and mixed (1:1) with various cryoprotectant solutions. The novel cryoprotectant solutions comprise standard dimethyl sulfoxide (DMSO) plus large molecular weight cryoprotectants. The cryoprotectant solutions evaluated included dimethyl sulfoxide (DMSO), polyvinylpyrrolidone (PVP), polythyleneglycol (PEG), and mixtures thereof. DMSO was utilized as the basic cryoprotectant, and evaluated at 0 M, 0.25 M, 0.5 M, and 1.0 M (final concentration). A cryoprotectant mixture comprising DMSO and PVP at 0%, 2.5%, 5.0%, 7.5%, and 10% (w/v) was evaluated to determine the optimal cryoprotectant mixture for this cell type. A cryoprotectant mixture comprising DMSO and PEG at 2%, 5%, 7.5%, and 10% (w/v) was evaluated also. For evaluation of cytotoxicity, platelet concentrates were mixed with cryoprotectants as noted above (1:1 ratio) and maintained at room temperature for two hours. Platelet function was then evaluated as noted infra. Graduated cooling experiments were conducted as described in Example 1, and platelet function tests as described above were conducted.

Figure 6:
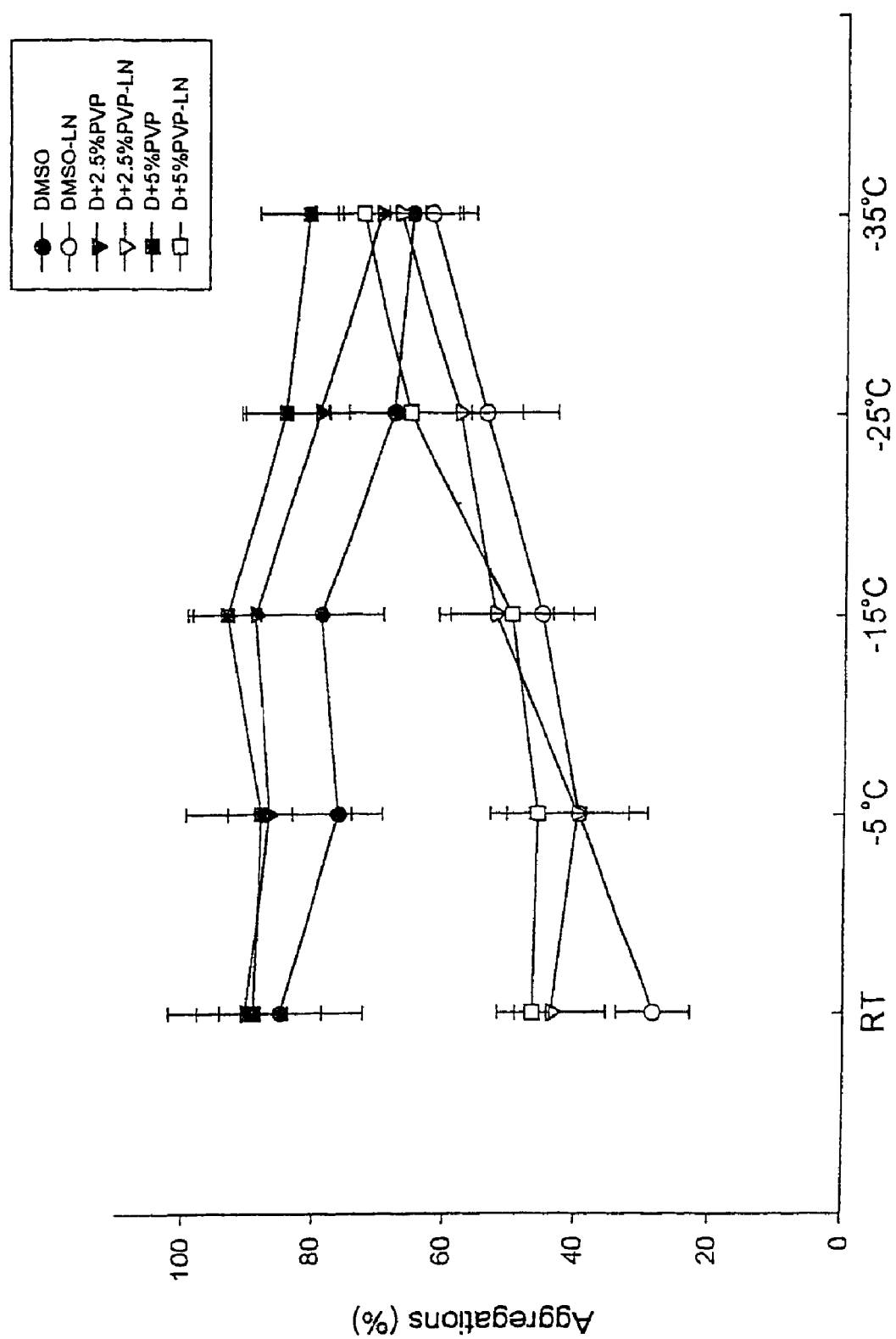
FIG. 6 shows platelet aggregation in the presence of varying compositions of cryoprotectant agent after freezing and thawing to various temperatures.
Figure 7:
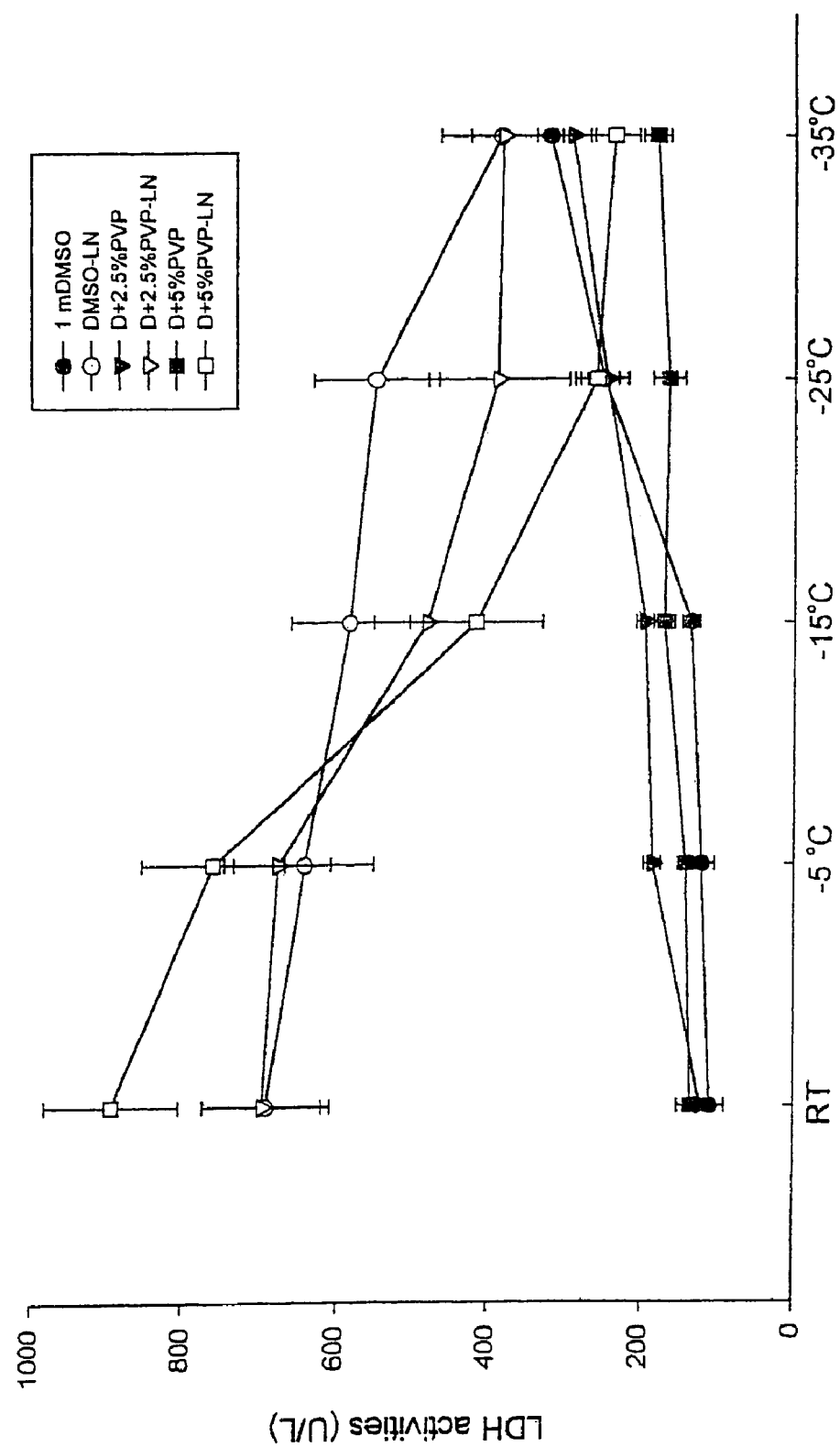
FIG. 7 shows platelet LDH release in the presence of varying compositions of cryoprotectant agent after freezing and thawing to various temperatures.
Figure 8:
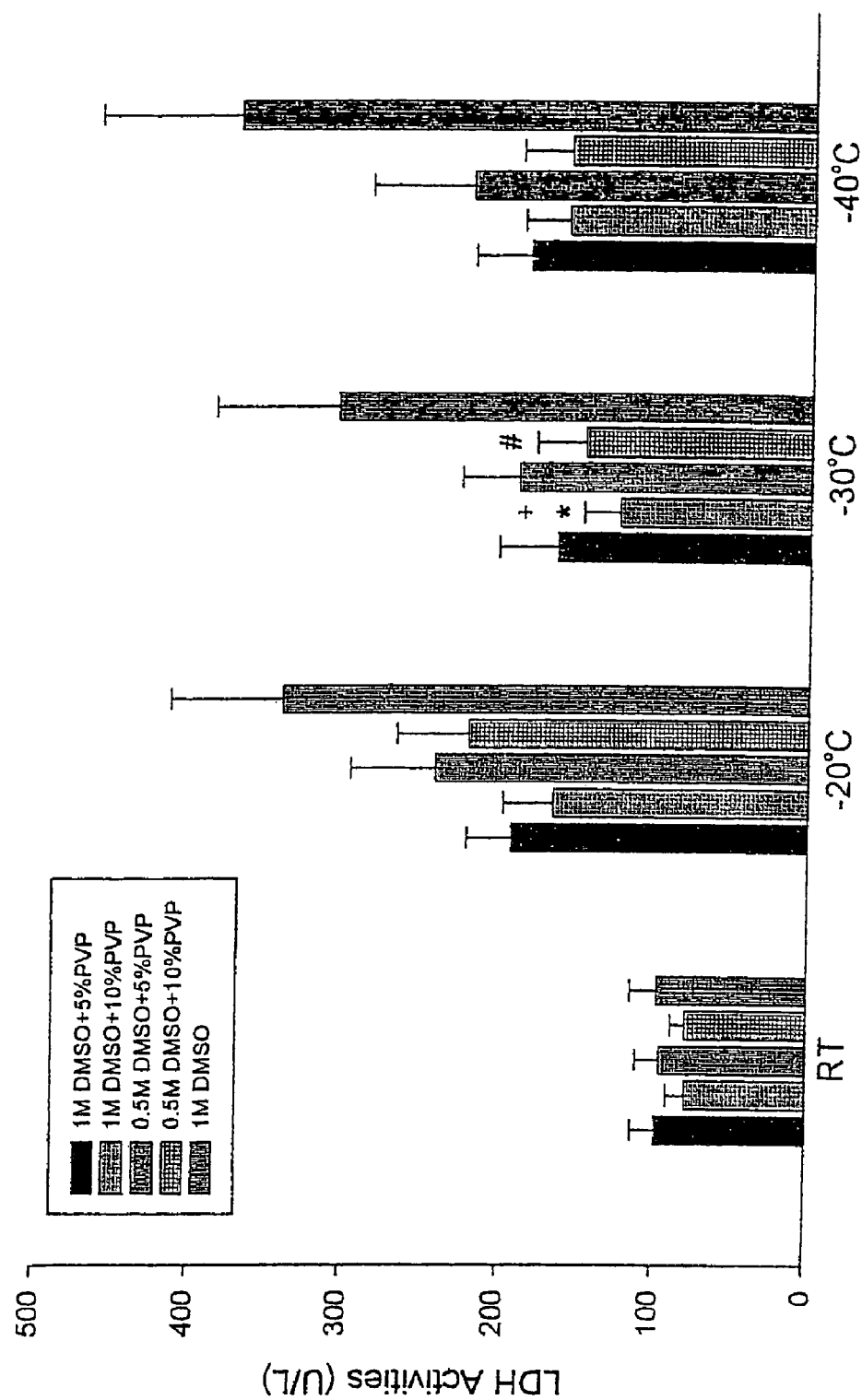
FIG. 8 shows platelet LDH release in the presence of varying combinations of DMSO and polyvinylpyrrolidine. *=$P<0.01$, #=$P<0.05$ compared to the −20 C group; +=$P<0.05$ compared to the −40 C group.

Addition of high molecular weight cryoprotectants to standard cryoprotective solutions (DMSO) improved functionality and membrane stability of cryopreserved platelets in comparison to DMSO alone. In particular, solutions comprising DMSO and 2.5% and 5% PVP improved platelet aggregation and reduced LDH release following cryopreservation (FIGS. 6 and 7). Similarly, cryopreservation solutions comprising 0.5 and 1 M DMSO and 10% PVP reduced LDH release (FIG. 8). Cryopreservation solutions comprising 0.5 M DMSO and 2% PEG gave good results in platelet aggregation tests following freezing, but tended to exhibit increased LDH release from platelets (not shown).

Figure 9:
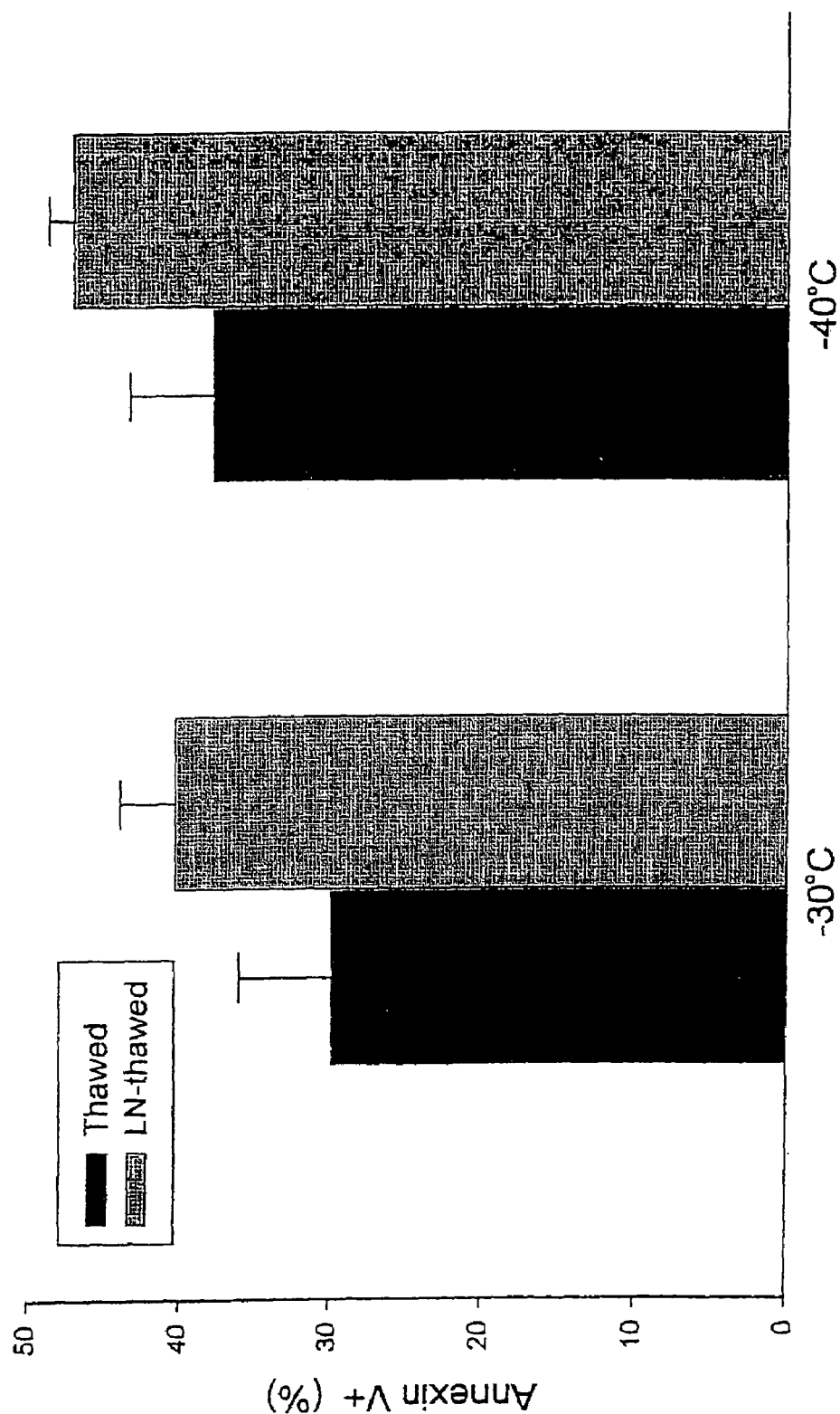
FIG. 9 shows platelet activation, measured as binding of Annexin V by flow cytometry, after freezing and thawing.

Addition of higher molecular weight cryoprotectants also reduced activation of platelets following freezing and thawing, determined as binding of Annexin V as measured by standard flow cytometric techniques for assessing binding of various antibodies (Gao et al., 1999. Cryobiology, 38: 225-235, incorporated herein by reference). In particular, a cryoprotective solution comprising 0.5 M DMSO and 10% PVP (w/v) was particularly effective (FIG. 9).

Figure 10:
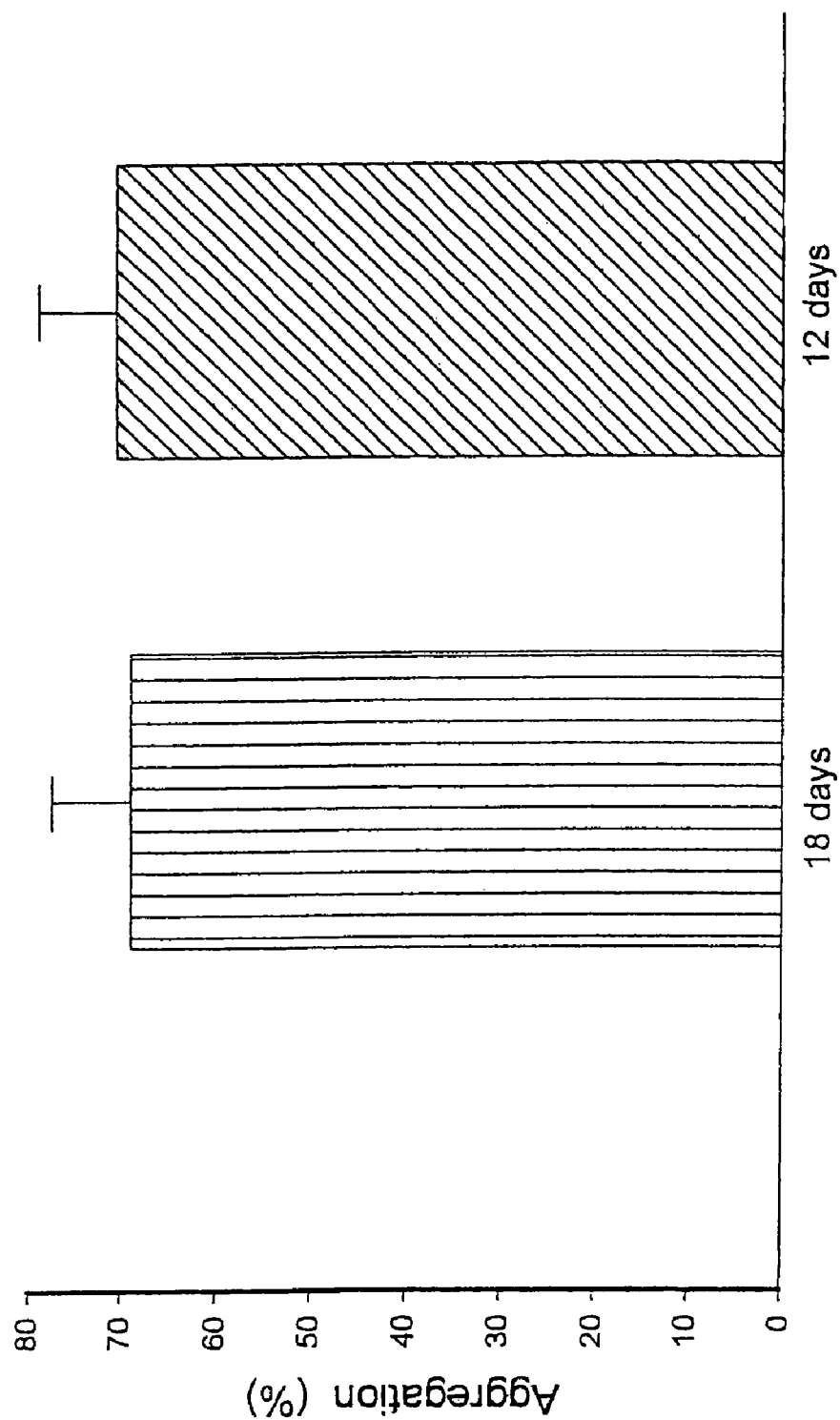
FIG. 10 shows platelet aggregation as a function of storage of cells in liquid nitrogen over time.

In separate experiments, effects of inclusion of large molecular weight cryoprotectants (0.5 M DMSO plus 10% polyvinylpyrrolidine) on long-term storage of platelets was evaluated. Platelet concentrates were cooled as described in Example 1 and transferred to liquid nitrogen for storage. As noted in FIG. 10, post-thaw platelet aggregation following frozen storage for 12 and for 18 days was essentially unchanged.

Accordingly, the methods and composition of the instant invention, comprising inclusion of large molecular weight cryoprotectants to standard cryoprotection solutions, have been found to be useful in preservation of membrane stability of fragile cell types such as platelets following freeze-thawing. The method is suitable for long-term cryopreservation of fragile cells such as platelets, and advantageously allows banking of such cells for future requirements. It will be appreciated that the methods and compositions of the present invention further have utility for bone marrow/cord blood hematopoietic progenitor cells for cancer treatment and gene therapy, for tissue cryopreservation for transplantation, for sperm/oocyte preservation for artificial insemination and in vitro fertilization, for cryopreservation of cell lines for research, and the like.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for cryopreservation of a cell, comprising:
    placing a cell in a bag including a cryoprotectant agent and placing the bag into a first container;
    placing the first container into a second container whereby an insulating space is defined between the first container and the second container;
    sealing the second container;
    gradually cooling the cell in cryoprotectant at a first cooling rate of from about 1° C./minute to about 3° C./minute by placing the bag in a first cooling device providing a first surrounding temperature of between about −60° C. to about −80° C. until a first temperature of the cell and cryoprotectant agent of between about −30° C. to about −80° C. is reached;
    wherein the first cooling rate is optimized for the cell type and controlled by the wall thickness of the second container and/or insulative properties of the first and/or second container; and
    transferring the sealed second container to a second cooling device providing a second surrounding temperature which is lower than the first surrounding temperature and is between about −80° C. to about −196° C.;
    whereby the cell placed in the first container is cryopreserved.

2. The method of claim 1, wherein the first container is fabricated of aluminum.

3. The method of claim 1, wherein the second container is fabricated of stainless steel.

4. The method of claim 1, wherein the cell is a platelet.

5. The method of claim 1, wherein the cryoprotectant is selected from a group consisting of dimethyl sulfoxide, polyvinylpyrrolidine, polyethylene glycol, and any mixture thereof.

6. The method of claim 1, wherein the first temperature of the cell and cryoprotectant agent is between about −30° C. to about −40° C.

7. The method of claim 5, wherein the cryoprotectant consists essentially of from about 0.5 M to about 1.0 M dimethyl sulfoxide and from about 5.0% (w/v) to about 15% (w/v) polyvinylpyrrolidine.

8. The method of claim 5, wherein the cryoprotectant consists essentially of from about 0.5 M to about 1.0 M dimethyl sulfoxide and from about 0.1% (w/v) to about 4.0% (w/v) polyethylene glycol.

* * * * *